United States Patent [19]
Wilson et al.

[11] Patent Number: 5,170,890
[45] Date of Patent: Dec. 15, 1992

[54] PARTICLE TRAP

[76] Inventors: Steven D. Wilson, P.O. Box 415, Soquel, Calif. 95073; William L. Clarke, 2221 Aralia St., Newport Beach, Calif. 92660

[21] Appl. No.: 622,845

[22] Filed: Dec. 5, 1990

[51] Int. Cl.⁵ .................................................. B07C 5/02
[52] U.S. Cl. .......................................... 209/301; 209/8; 209/11; 209/606; 209/127.2; 250/251
[58] Field of Search .................. 209/3.1, 3.3, 579, 606, 209/127.2, 4, 8, 11; 250/251

[56] References Cited
U.S. PATENT DOCUMENTS

| | | | |
|---|---|---|---|
| 3,710,279 | 1/1973 | Ashkin | 250/251 X |
| 3,778,612 | 12/1973 | Ashkin | 250/251 |
| 3,808,550 | 4/1974 | Ashkin | 250/251 X |
| 4,025,787 | 5/1977 | Janner et al. | 250/251 |
| 4,115,078 | 9/1978 | Janner et al. | 250/251 X |
| 4,327,288 | 4/1982 | Ashkin et al. | 250/251 |
| 4,366,379 | 12/1982 | Cotter | 250/251 X |
| 4,887,721 | 12/1989 | Martin et al. | 209/606 X |
| 4,893,886 | 1/1990 | Ashkin et al. | 359/350 X |

FOREIGN PATENT DOCUMENTS 0988378  1/1983  U.S.S.R. ............................. 209/579

Primary Examiner—Donald T. Hajec
Attorney, Agent, or Firm—Jeffrey A. Hall

[57] ABSTRACT

An invention is described in which a method and apparatus are disclosed for guiding, trapping, concentrating and separating particles. The method comprises containing particles in a gas, liquid, or other fluid medium, projecting a beam of light into the particles, inducing the beam of light to impart a spinning motion to the particles, generating a field density gradient in the fluid medium thereby trapping the particles in the beam of light, guiding the particles on the beam of light, concentrating the particles at a focal plane of the beam, and if desired, separating the particles into groups by size and density. Particles are caused to spin and interact with the energy gradient of the beam of light, causing them to orbit in a controlled manner. A preferred apparatus utilizes a chamber, a switching mechanism under a vacuum or partial vacuum, a light source such as a laser or a plurality of lasers, and a lens or a plurality of lenses may be used. Other embodiments utilize various light sources with or without lenses.

16 Claims, 2 Drawing Sheets

PARTICLE TRAP

BACKGROUND OF THE INVENTION

1. Field of the Invention

This invention relates generally to methods and apparatuses wherein material particles are caused to rapidly spin by interaction with intense beams of light. The interaction of the spinning particles with the energy gradient of the light beam or surrounding fluid causes the particles to orbit in a controlled manner leading to new apparatuses for guiding, trapping, concentrating, separating, injecting, and analyzing particles.

2. Description of Prior Art

The present invention encompasses an apparatus for the exploitation of an anomalous interaction (force) between the gradient field density and a particle spin induced by an intense beam of light. Such interaction can dominate the visual light pressure and cause micron to submicron sized particles to be attracted to a beam focus against the direction of the propagating vector of the light.

Such phenomena is observed at several different length and time scales in a number of different environments, i.e., micron-sized particles in air or other gasses, liquids, or other fluids, angstrom-sized particles in such varying environments is a fundamental feature of this invention. For example, for a micron-sized particle in a partially evacuated chamber, a laser may be used to induce a rapid spinning motion of a particle. In such high Reynolds' number fluid dynamical regime, the particle induces a turbulent vortex motion which interacts with the density gradient of the fluid caused by the localized heating of such fluid by the beam.

When such beam is focused down to a small spot size, for example 3-10 microns, the spinning particles are observed to spiral into the focal plane and become trapped by such spin-gradient force operating in both transverse directions and longitudinally. The present invention utilizes such spin-gradient interacting force to guide, trap, concentrate, and control particles. Secondary effects of such interaction may also be exploited. An example of such secondary effect is the separation of such particles according to their sizes and densities as they become trapped or repelled commensurate with the strength of an applied vacuum and strength of an applied energy source.

There is no prior art known to applicant in which such anomalous interaction (force) between the gradient of a field density and a particle spin induced by a beam of light is utilized to guide, trap, concentrate, separate, or control the motion of particles.

SUMMARY OF THE INVENTION

The present invention encompasses a method and apparatuses for applying such method to exploit an anomalous interaction force between the gradient of a field density and a particle spin induced by a beam of light to guide, trap, concentrate, separate or control particles. The light source may be coherent or noncoherent. Alternatively, other sources of energy may be used to induce such particle spin or dipole moment.

A method where a light beam is focused on particles so as to cause micron and sub-micron sized particles to be attracted to such beam, against the direction of the propagating vector of the light; if the light source is from an incandescent light the particles spiral towards the focal plane; if the light source is a laser beam the particles stream back and forth. In both cases, particles become trapped in the focal plane and particles on the outer edge oscillate both toward and a way from the focal plane while being repelled back by the particles near it.

One embodiment of the invention comprises a light source means, a focusing lens, a partially evacuated chamber, and means to inject particles into said chamber. When such particles are injected into said chamber the particles initially form an electrostatically charged cloud. The heating effect of the light beam causes the particles at the edge of the beam to be heated on one side more than on the other side resulting in a rapid spinning motion imparted to the particle. The overall effect is a force which tends to repel the particles from regions of higher fluid density (i.e. lower temperature) in both transverse directions and along the beam axis (longitudinal direction). Balancing repulsive forces therein causes the particles to orbit into the focus of the beam, where they are trapped. Furthermore, because such spinning particles induce stable vortex rings near the focal plane of the beam, such particles will tend to clump into separated series of spinning particle clouds.

Another embodiment comprises this methodology applied in an apparatus where the light source is an intense collimated Gaussian beam focused on particles given an initial spin and orbital velocity and projected into said beam by an injector. In this embodiment the transverse spin-gradient force will guide and constrain such particles to spiral orbits along the beam. This embodiment is useful as a particle guide and injector.

Accordingly, I claim the following as the objects and advantages of the invention: to provide a method and apparatus for applying the same to trap, separate, concentrate and inject particles into living and non-living media; to provide such a method and apparatus useful for the separation and identification of macromolecules; to provide such a method and apparatus useful for the separation and injection of genetic material into cell nuclei; to provide such a method and apparatus useful for the purification of organic molecules.

Further objects are to provide a method and apparatus for trapping and guiding particles in a collimated beam for injecting macromolecules into cells, injecting dopants into semiconductors, injecting seed crystals into a melt, injecting samples into a cell for analysis by FTIR, NMR, neutron activation, and the like, and for injection of fusion pellet for bombardment.

Still further objects include to provide a method and apparatus for concentrating particles for the purification of metals and the plating of materials on metals, to provide such a method and apparatus for concentrating chemical agents, and to provide such a method and apparatus for controlled mixing of heterogeneous particles.

In addition I claim the following additional objects and advantages of the invention: to provide a method and apparatus for weighing and measuring particles, to provide a method and apparatus for measuring dielectric properties, to provide a method and apparatus for measuring heat conductivity, to provide a method and apparatus for measuring the viscosity of gases, and to provide a method and apparatus for measuring the collimation of a laser.

The trapping, separation, guiding, concentrating, and controlling particles using such method and apparatus is applicable in a wide variety of fields. For example:

1. In fusion technology it would be very advantageous to be able to control the position and direction of a heavy hydrogen pellet so as to facilitate a higher target yield.

2. The separation of micron-sized particles by controlling the amount of vacuum in the apparatus would be very useful for purification of elements or cellular components, and liquid phase structuring.

3. Various impurities could be induced or disintegrated within a sample by controlling the frequency and power of the light beam, for example, a laser, thereby inducing magnetic fields or electric fields and controlling the spin of the particle.

4. Such method and apparatus could be used in the form of a plasma gun by trapping palladium hydride pellets then targeting them with a high powered laser in a cross field and controlling the direction by vacuum release.

5. Other applications of such method and apparatus include the generation of highly charged positive ions, or providing means to power a space thrust engine by variation in the configuration and frequencies of the applied vacuum.

Further objects and advantages of the invention will be apparent from a consideration of the ensuing description and accompanying drawings.

DETAILED DESCRIPTION OF THE PREFERRED EMBODIMENT OF THE INVENTION

Figure 1:
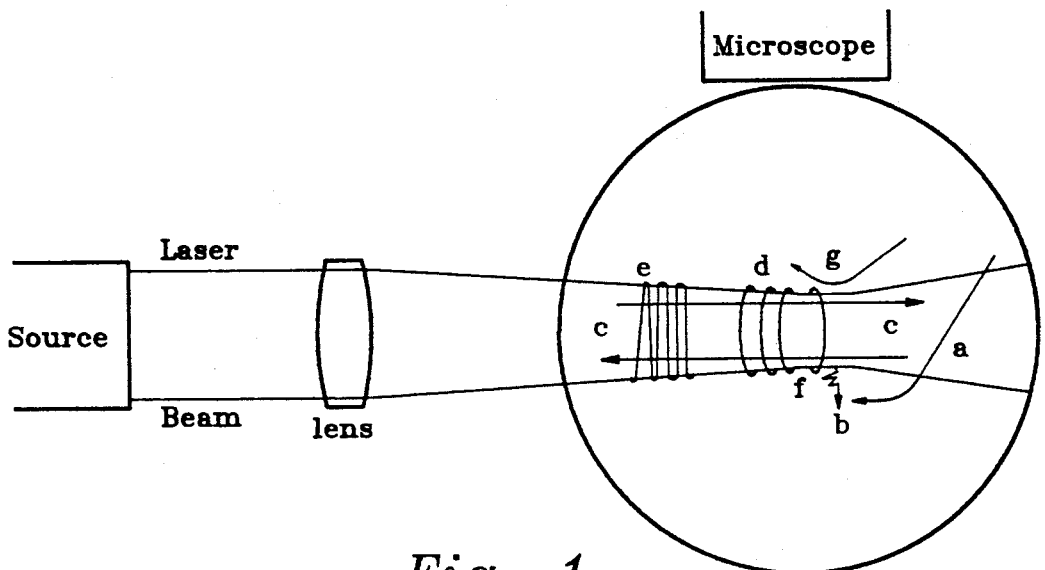
FIG. 1 is an illustration of light affecting particles in a partial vacuum or liquid medium according to the method and apparatus of the invention.

The present invention encompasses a method and apparatus to exploit an anomalous interaction (force) between the gradient of a field density and a particle spin induced by a beam of light. Such interaction can dominate the visual light pressure and cause micron and submicron sized particles to be attracted to a beam focus, against the direction of the propagating vector of the light.

The preferred embodiment of the invention comprises a method and apparatus for guiding, trapping, separating, and controlling particles. The method comprises containing particles in a vacuum, liquid, or other fluid medium, projecting a beam of light onto said particles, inducing said beam of light to impart a spinning motion to said particles, inducing said beam of light to impart a dipole moment to said particles, generating a field density gradient in said vacuum, and then trapping the particles in the beam, guiding the particles on the beam, concentrating the particles at a focal plane of the beam, and then separating the particles into groups by size and density.

The vacuum may be a partial or a full vacuum. The beam of light may be coherent or noncoherent, or the spinning motion of said particles may be induced by a circularly polarized beam of light. The field density gradient is preferably a mass density gradient of a gas or liquid caused by local heating of the gas or liquid by a beam of light. To induce spinning motion of the particles, the particles are preferentially induced to spin by differential heating of the particles by a beam of light.

Alternatively, the field density gradient may be the electric field vector strength of a light beam in the partial or full vacuum. Trapping and guiding of the particles may be accomplished by controlling an interaction between a spinning particle and a mass density gradient effectuated by a local heating by said beam of light in a transverse direction. In another embodiment trapping and guiding particles in a beam of light is accomplished by interacting particles having a dipole moment induced by a beam of light and an electric field density gradient of the beam of light operating in a substantially transverse direction.

Concentrating particles is preferably induced at a focal plane of said beam of light and is accomplished by an interaction between the spinning article and a mass density gradient caused by a focused local heating of said beam of light in an essentially longitudinal direction. In another embodiment the particles are concentrated at a focal plane of the beam of light by an interaction between an induced dipole moment of said particles and an electric field density gradient of a focused beam of light in a generally longitudinal direction.

The separation of particles is preferably effectuated by controlling a balance between an electrostatic repulsion between the particles and a magnetic attraction between a magnetic field and a vortex field generated in the medium by charged, spiralling particles therein. Alternatively, in another embodiment of the invention the separation of particles is accomplished by inducing a dipole moment and a magnetic moment in the particles with a circularly polarized beam of light and controlling a balance between a repulsion of like ionized particles therein and the magnetic attraction between the particles magnetic moments so as to effect a separation of said particles thereby.

An apparatus according to the invention for controlling guiding, trapping, and separating, particles comprises means for containing particles in a vacuum, liquid, or other fluid medium, means for projecting a beam of light onto said particles, means for inducing said beam of light to impart a spinning motion to said particles, means for inducing said beam of light to impart a dipole moment to said particles, means for trapping the particles in the beam of light, means for guiding the particle on the beam of light, means for concentrating the particles of the focal plane of the beam of light, and means for separating the particles into groups by size and density.

The utilization of the anomalous interaction force between the gradient of the field density and a particle spin induced by a beam of light is possible in various regimes, i.e., micron-sized particles in air, gasses, liquids or other fluids, angstrom-sized particles in a vacuum, etc. It is a principal utility of the invention to provide control of the motion of particles in all these regimes and at the interface of these regimes. For example, for micron-sized particles using a partially evacuated chamber, a laser is preferably used to induce a rapid spinning motion of a particle or a plurality of particles. In such high Reynolds' number fluid regime, such particle or particles induce a turbulent vortex motion which interacts with the density gradient of the fluid caused by the localized heating of the fluid by the beam. The particle is thus trapped in the beam spin-gradient force, i.e. the interaction between the spinning particle and the density field gradient of the fluid. The exploitation of this spin-gradient force by the method and apparatus provided herein enables the user to trap, guide, separate, concentrate, and control particles in novel and heretofore unattainable manner.

At atomic dimensions, such spin-gradient force may also be utilized. Here the particles are subject to a vacuum in a circularly polarized beam. Such beam induces a dipole moment in the outer electron shell of the atomic particle which interacts with the gradient of the electric field vector of the polarized beam. This results in a pondermotive force which attracts the particles to the center and focal plane of the polarized beam, thereby trapping them. Furthermore, the circularly polarized beam induces a magnetic moment similar to those observed in a paramagnetic spin system.

Such spin-gradient force may be utilized for guiding, trapping, concentrating, separating, and controlling macro-sized particles, micron-sized particles, and subatomic sized particles using the method and apparatuses described herein.

FIG. 1 illustrates light affecting particles in a partial vacuum, liquid or other fluid medium as applied according to the method and apparatus of this invention. If the light source is from an incandescent light the particles (a) spiral towards the focal plane; whereas if the source is a laser beam the particles (c) stream back and forth. In both cases, particles become trapped in the focal plane (f) and particles on the outer edge (e) oscillate toward and away from the focal plane being repelled back by the particles near it. The particle or particles near (d) or at the focal plane (f) will remain in position as they rotate in the light's aixs as well as rotate on their own axis. Particles entering near the focal plane (b) oscillate and become trapped, while those approaching (g) are repelled. The above qualitative dynamical behavior of the particles in a gas, or liquid medium is similar.

Figure 2:
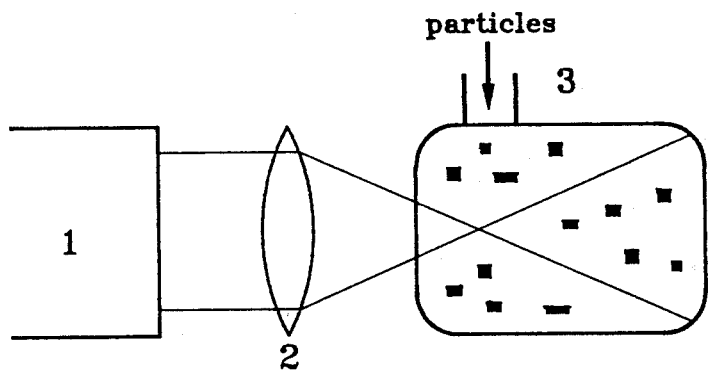
FIG. 2 shows a schematic view of a particle trap according to the invention.

FIG. 2 shows another embodiment of the invention utilizing an apparatus having an intense light source 1, preferably a coherent laser source, and a focusing lens 2 for focusing the beam into a partially evacuated chamber 3. Using such apparatus when micron-sized particles are injected into the chamber, such particles initially form an electrostatically charged cloud. Due to the intense heating affect of the beam on the particles, the particles at the edge of the beam are heated on one side to a far greater extent than on the other side. This differential heating results in inducing the particle to rapidly spin. For example, the thermo-gradients that are generated by the radiation of the laser beam, i.e. using a 100 MW laser with a spot diameter of $8.06\mu$ its intensity is 63 milliwatts. This is equivalent to:

$15.06 \times 10^{-2}$ cal sec or 0.063 joules/sec. or $63 \times 10^4$ ergs/sec.

A surface of a flake-like graphite particle, for example, would absorb a fraction of the total incident radiation, i.e.;

$9.918 \times 10^{-4}$ cal/sec or equivalent to $4.15 \times 10^4$ ergs/sec., which is sufficient to heat up one surface more than the other. Such differential heating affect is termed photophoresis, and is caused by the increased pressure on the heated part of the particle by the surrounding air molecules, as described by the ideal gas law:

$P = nRT/v$ wherein n, R, and V are constant, and T is higher for the air near the heated side of the particle. The uneven pressure on the article causes it to spin, such spin being a direct photophoresis. This photophoresis effect will also be evident for particles in a liquid medium.

Particles outside of the beam of light as well as particles completely inside of the beam of light are seen to drop out by the force of gravity in the chamber. Only particles on the edge of the light beam which are rapidly spinning are supported by the lift effect of the spin and are trapped within the beam. Such particles have a pitch angle, and because the fluid is much hotter inside the beam, a propeller effect results which forces the particle to orbit in a spiral motion towards the center, on either side of the focus, i.e. even against the direction of the beam of light.

The spinning particle induces a vortex motion in the surrounding fluid which causes the particle to be repelled by the cooler and denser fluid outside of the beam of light, and by the cooler and denser fluid further away from the focus. This is illustrative on one aspect of the aforementioned spin-gradient force, i.e. an interaction between the spinning particle and induced vortex, and the density gradient of the air caused by the local heating by the beam.

Using a laser beam, the energy density $E^2/4\pi$ rapidly diminishes at the edges thereof, therefore:

$\partial E / \partial X$ is large.

Figure 3:
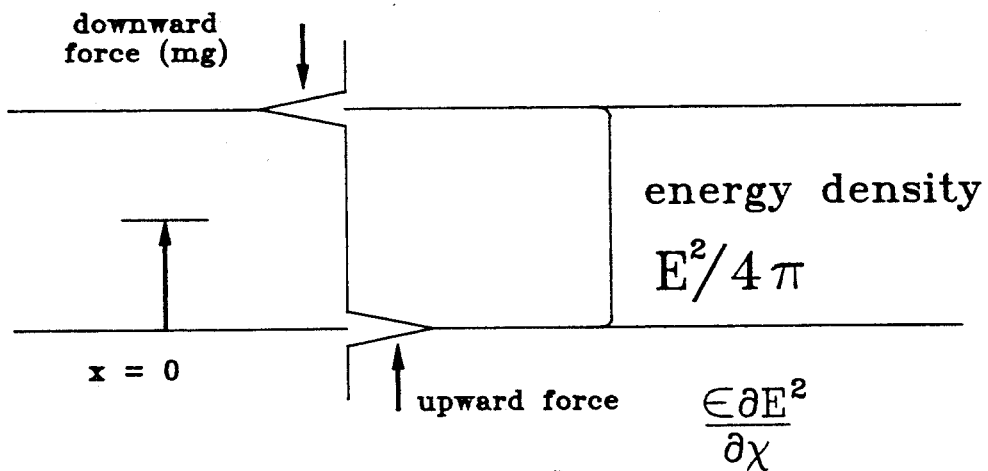
FIG. 3 shows a schematic illustration of the energy density of a laser beam which may be used as a light beam source according to the invention.

Referring to FIG. 3 if $\epsilon \partial E / \partial X > mg$, the upward force depicted in FIG. 3, the particle will be suspended.

If $\epsilon \partial E / \partial X < mg$, then the particle will drop out of the beam, where m=mass of the particle and g=the gravitational acceleration. In a hard vacuum the particle, typically having a small velocity $V_t = mg/\mu$ where t=the geometry factor and $\mu$=the viscosity of the air, has instead an energy of $\frac{1}{2}mv^2 = mgh$. If $mgh = \frac{1}{2}mv^2$ is greater than $\frac{1}{2}\epsilon E^2$ t then the particle will drop out of the beam. Conversely, in a soft vacuum i.e. pressure of from 10 to 2 mm of mercury, if $mg/\mu = V_t$ is less than $\frac{1}{2}\epsilon E^2$ then the particles should remain suspended.

In the above example, the description of the forces responsible for the suspension of particles upward force must be greater than the weight of the particle in a partial vacuum. For example, a force of $2.97 \times 10^{-2}$ dynes is needed for the largest particle and the influence of $V_t$ is equal to $3.66 \times 10^{-16}$ cm/sec. Then when a hard vacuum is a particle having a mass of $6.5 \times 10^{-12}$ gm., for example, must have a velocity exceeding 31.5 cm/sec. or a K.E. $1.32 \times 10^{-8}$ ergs to break through the bottom barrier of the laser beam.

Figure 4:
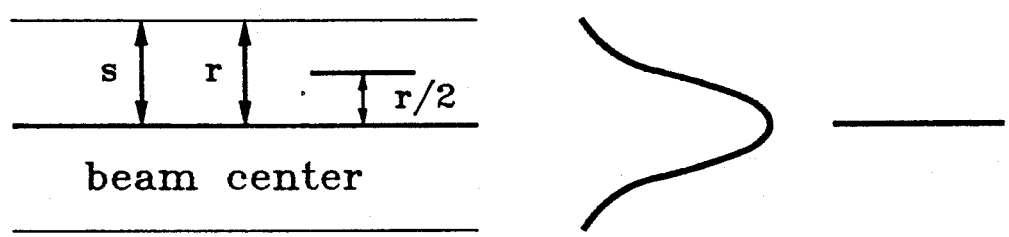
FIG. 4 shows a schematic illustration of the density barrier of a Gaussian laser beam as applied in a partial vacuum or liquid according to the invention.

Referring to FIG. 4 the trapping of particles by a beam is strongly dependent on the use of a Gaussian laser beam having a sharp boundary and applied in a partial vacuum. Such application causes a sharp temperature, and therefore a density gradient. The overall effect is a force which tends to repel the particle from regions of higher fluid density, that is lower temperature, in both transverse directions and along the beams axis in a longitudinal direction. The resultant vortex motion is a known is effect of systems obeying the Navier-Stokes equations for a viscous fluid. In tensor form there are:

$$\frac{Dui}{Dt} = \frac{\partial ui}{\partial t} + uj \frac{\partial ui}{\partial uj} =$$

$$-\frac{\partial p}{\rho \partial xi} + \frac{\mu \partial^2 ui}{\partial x^2 i} + \frac{\mu}{3} \frac{\partial}{\partial xi}\left(\frac{\partial ui}{\partial xi}\right)$$

where $$\frac{Dui}{Dt}$$

is the time velocity rate of change change of the velocity of a fluid with velocity vector ui
 $\rho$ = is the fluid density
 $\mu$ = is the fluid viscosity.

Balancing these repulsive forces in the transverse direction is the centripetal force caused by the orbiting particle. The particle motion is constrained to orbit in a spiral around the edge of the beam by the balance between the spin gradient and the centripetal forces.

Figure 5:
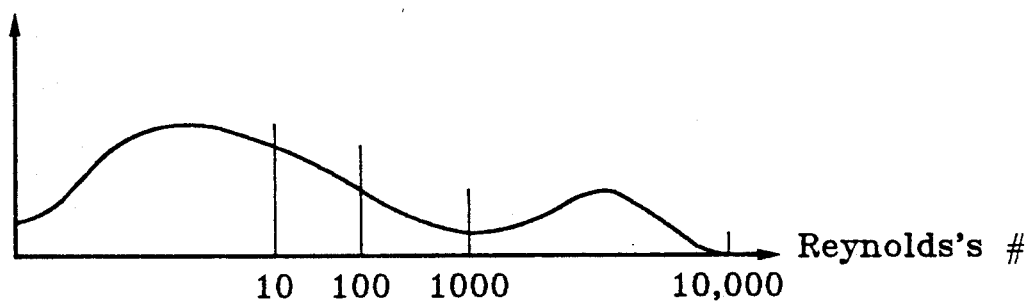
FIG. 5 shows the negatively sloped coefficient of viscosity or negative resistance, illustrating how a rapidly spinning particle will favor a trajectory which makes the particle spin the fastest, i.e. on the edge of the applied beam, according to the invention.

Such effect is also related to an important non-linear effect, namely to the negatively sloped coefficient of viscosity or negative resistance. For rapidly spinning particles i.e. those with a Reynolds number between approximately 10 and 100, a trajectory will be favored which makes the particle spin the fastest, for example, on the edge of the applied beam of light as illustrated in FIG. 5.

The resultant balance of such forces causes the particles to orbit into the focus of the beam, where they are trapped. As such the apparatus functions as a particle trap. Furthermore, because the spinning particles induce stable vortex rings near the focal plane of the beam, the clouds of particles will tend to clump into a separated series of spinning clouds.

Figure 6:
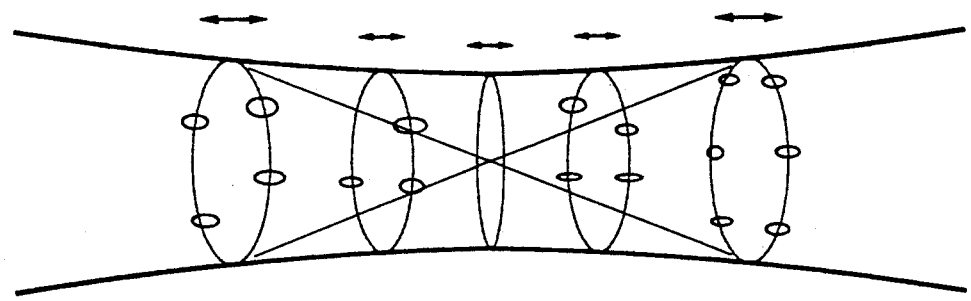
FIG. 6 shows a uniform distribution of particles in vortex ring configuration orbiting the waist of a light beam with successive clouds spinning in opposite directions according to the invention.

Referring to FIG. 6 shows the final step or condition of the system. Here the particles have grouped themselves into multiple clouds orbiting around the waist of the beam. Successive clouds are spinning in opposite directions, causing the clouds to repel one another. Furthermore, because the individual particles carry like electrostatic charges, they are uniformly distributed in each vortex ring.

The balance between this repulsion between vortex clouds and the aforementioned spin-gradient or trapping force in the longitudinal direction causes the clouds to oscillate along the beam axis. The smaller and lighter and generally more rapidly spinning particles will group closer to the focus, and the larger and more massive particles will orbit further away from the focus. These are the aforementioned secondary effects which allow the particle trap of FIG. 2 to also function as an analyzer of particle sizes and masses. As the particles carry a surface charge and are rapidly spinning, they will also interact with each other by means of their magnetic fields. This will cause further secondary effects which may allow the particles to be separated based on their dielectric properties.

In another embodiment an apparatus exploiting such spin-gradient force comprises a light source which is preferably an intense collimated Gaussian beam, so as to provide spin-gradient forces in a transverse direction, but not in a longitudinal direction. An injector provides an initial spin and orbital velocity, and particles are injected into the collimated beam. The transverse spin-gradient force will guide and constrain the particles to spiral orbits along the beam. Therefore the preferred application of such apparatus is as a particle guide and injector.

Such spin-gradient force may also be utilized with atomic-sized particles in a partial or in a complete vacuum. Preferably a circularly polarized light beam is used to induce a rotating dipole moment in the outer negatively charged electron shells of the atomic particles which interact directly with the rotating electric field gradient of the beam of light. The particles will orbit in a manner as described above and they will be attracted towards the point of maximum electric field energy, i.e., towards the center of the beam of light in the transverse direction and towards the focal point along the beam axis.

If a laser is used as a light source, and such laser is tuned far from any resonant absorption band of the atomic particles, this rotating induced dipole-field gradient force will dominate over the photon pressure caused by resonant absorption. Therefore apparatus similar to those illustrated in FIG. 2 and described above, may also be utilized to trap, separate, and guide atomic particles. Such particles are attracted to the abovementioned spin-gradient force and such functions are then readily implemented. The spin-gradient force will balance the centripetal force of the orbiting particles and such particles may then be manipulated and guided while trapped in the beam. A microscopic analog of such nonlinear negative resistance will be obtained in the ionized channel of the beam. Generally, multiple particle orbits at different distances from the optical axis will occur close to the edge of the applied beam.

In another embodiment of the invention a laser is utilized and focused on a plurality of accelerated spinning ions contained within a vacuum, partial vacuum, or other fluid medium. An ionized channel forms created by the laser beam and the spin-gradient force is then utilized according to the methodology of the invention to guide a beam of ionized particles through the ionized channel.

While the above description contains many specificities they should not be construed as limitations on the scope of the invention, but merely as exemplifications of preferred embodiments thereof. Those skilled in the art will envision many other possible variations are within its scope. The interrelation and control of the various forces and effects described herein provide a means for trapping and guiding any material particle by exploitation of the interaction between the spinning particles and a field gradient. The asymptotic stability of the system will be determined by the non-linear effects in a fluid or ionized channel, or within the variation of an induced dipole moment in the particles. Such method and apparatus as described herein provides a means to exploit the non-linear spin-gradient force to control, guide, trap, separate, and control particles or a plurality of particles having a wide variety of sizes, weights, and physical properties. Moreover, particles trapped in a laser beam, for example, in a liquid, behave similarly as that in a gas, albeit with a slight diminution of motion. Accordingly, the scope of the invention should be determined by the appended claims and their legal equivalents, and not by the examples which have been given.

We claim:

1. A method for guiding, trapping, separating, and controlling particles comprising:
   containing particles in a vacuum,
   projecting beam of light onto said particles,
   inducing said beam of light to impart a spinning motion to said particles,
   inducing said beam of light to impart a dipole moment to said particles,
   generating a field density gradient in said vacuum,
   trapping the particles in the beam of light,
   guiding the particles on the beam of light,
   concentrating the particles at a focal plane of the beam of light, and
   separating the particles into groups by size and density.

2. The method of claim 1 wherein said vacuum is a partial vacuum.

3. The method of claim 1 wherein said vacuum is a full vacuum.

4. The method of claim 1 wherein said beam of light is a focused beam of light.

5. The method of claim 1 wherein said beam of light is a collimated beam of light.

6. The method of claim 1 wherein said field density gradient is a mass density gradient of a gas or a liquid fluid medium caused by local heating of said fluid by a beam of light.

7. The method of claim 6 wherein said spinning motion of said particles is induced by differential heating of the particles by a beam of light.

8. The method of claim 1 wherein said field density gradient is an electric field vector of a light beam in a vacuum.

9. The method of claim 8 wherein said dipole moment and said spinning motion of said particles is induced by a circularly polarized beam of light.

10. The method of claim 1 wherein said trapping and said guiding of said particles further comprises an interaction between a spinning particle and a mass density gradient effectuated by a local heating by a beam of light in a transverse direction.

11. The method of claim 10 wherein a concentration of particles at a focal plane of said beam of light is provided by an interaction between a spinning particle and a mass density gradient actuated by a focused local heating of said beam of light in a longitudinal direction.

12. The method of claim 11 wherein a separation of said particles is effectuated by controlling a balance between an electrostatic repulsion between the particles and a magnetic attraction between a magnetic field and a vortex field generated in said medium by charged, spiralling particles therein.

13. The method of claim 12 wherein a separation of said particles is effectuated by controlling a balance between the electrostatic and vortex repulsion between the particle clouds and the spin-gradient trapping force in the longitudinal direction.

14. The method of claim 6 wherein said trapping and guiding of particles in said beam of light is actuated by interacting particles having a dipole moment induced by the beam of light and an electric field density gradient of the beam of light operating in a substantially transverse direction thereto.

15. The method of claim 14 wherein said particles are concentrated at a focal plane of said beam of light by an interaction between an induced dipole moment of said particles and an electric field density gradient of a focused beam of light in a longitudinal direction thereto.

16. The method of claim 15 wherein said particles are separated by inducing a dipole moment and a magnetic moment in said particles with a capacity polarized beam of light, and controlling a balance between a repulsion of like ionized particles therein and a magnetic attraction between said particles magnetic moments so as to effect a separation of said particles thereby.

* * * * *